United States Patent
Kutsch et al.

(10) Patent No.: US 9,849,310 B2
(45) Date of Patent: Dec. 26, 2017

(54) DENTAL APPLIANCE, ORAL CARE PRODUCT AND METHOD OF PREVENTING DENTAL DISEASE

(75) Inventors: V. Kim Kutsch, Albany, OR (US); Robert J. Bowers, Albany, OR (US); Graeme Milicich, Hamilton (NZ); Jesse L. Droesch, Albany, OR (US)

(73) Assignee: DENTAL ALLIANCE HOLDINGS, LLC, Albany, OR (US)

( * ) Notice: Subject to any disclaimer, the term of this patent is extended or adjusted under 35 U.S.C. 154(b) by 778 days.

(21) Appl. No.: 12/456,849

(22) Filed: Jun. 23, 2009

(65) Prior Publication Data

US 2009/0324662 A1   Dec. 31, 2009

Related U.S. Application Data

(60) Provisional application No. 61/133,098, filed on Jun. 24, 2008.

(51) Int. Cl.
| | | |
|---|---|---|
| *A61K 8/02* | (2006.01) | |
| *A61K 8/00* | (2006.01) | |
| *A61K 8/97* | (2017.01) | |
| *A61Q 11/00* | (2006.01) | |
| *A61K 8/34* | (2006.01) | |

(52) U.S. Cl.
CPC ............. *A61Q 11/00* (2013.01); *A61K 8/345* (2013.01)

(58) Field of Classification Search
USPC ......................................................... 424/49
See application file for complete search history.

(56) References Cited

U.S. PATENT DOCUMENTS

| | | | |
|---|---|---|---|
| 3,970,747 A * | 7/1976 | Barth .................. A61K 8/345 424/49 | |
| 4,150,151 A | 4/1979 | Pader et al. | |
| 4,372,978 A | 2/1983 | Gilbertson et al. | |
| RE31,815 E | 1/1985 | Alfano | |
| 5,213,615 A | 5/1993 | Michl | |
| 5,738,113 A | 4/1998 | Connely | |
| 5,770,182 A * | 6/1998 | Fischer ........................... 424/49 | |
| 5,804,165 A * | 9/1998 | Arnold ........................... 424/44 | |
| 6,036,943 A * | 3/2000 | Fischer .................... A61C 5/00 424/49 | |
| 6,043,047 A | 3/2000 | Foote et al. | |
| 6,314,960 B1 * | 11/2001 | Vines .......................... 128/859 | |
| 6,342,207 B1 | 1/2002 | Stoor et al. | |
| 6,375,934 B1 | 4/2002 | Eklund et al. | |
| 6,484,144 B2 | 11/2002 | Martin et al. | |
| 6,548,018 B2 | 4/2003 | DiCesare et al. | |
| 6,685,921 B2 | 2/2004 | Lawlor | |
| 6,846,478 B1 | 1/2005 | Doyle et al. | |
| 2002/0114768 A1 | 8/2002 | Stoor et al. | |
| 2003/0205234 A1* | 11/2003 | Bardach .............. A61C 19/063 128/861 | |
| 2005/0025720 A1 | 2/2005 | Bailey | |
| 2005/0100866 A1 | 5/2005 | Arnone et al. | |
| 2005/0142074 A1 | 6/2005 | Pushpangadan et al. | |
| 2005/0169852 A1 | 8/2005 | Roberge et al. | |
| 2005/0191247 A1 | 9/2005 | Drake et al. | |
| 2008/0057531 A1* | 3/2008 | Machida et al. ................ 435/32 | |
| 2012/0321570 A1 | 12/2012 | Kutsch et al. | |

OTHER PUBLICATIONS

Mackley, Peter, Biofilms and caries, Australasian Dentist, www.essology.com, pp. 60-61.*
Featherstone et al., Caries Management by Risk Asessment: Consensus Statement, Apr. 2002, J. of California Dent. Assoc., 2003, p. 1-8.*
Kutsch, "Dental Caries: a biofilm disease." Dental Practice: Sep./Oct. 2006; 184-190.*
U.S. Appl. No. 11/337,435, May 30, 2014, Office action.
U.S. Appl. No. 11/337,435, April 17, 2015, Office action.
U.S. Appl. No. 11/337,435, Oct. 15, 2015, Office action.
U.S. Appl. No. 11/337,435, Jan. 5, 2016, Office action.
U.S. Appl. No. 13/080,644, Nov. 21, 2012, Office action.
U.S. Appl. No. 13/080,644, Oct. 3, 2014, Office action.
U.S. Appl. No. 13/080,644, May 8, 2015, Office action.
U.S. Appl. No. 13/080,644, Oct. 16, 2015, Office action.
Rethman, Jill, Trends in Preventative Care Caries Risk Assessment and Indications for Sealants, JADA, vol. 131, Jun. 2002.
Google printout Feb. 21, 2004 searching Kutsch and Chicago Midwinter (six page search printout.
Davidson et al, Evaluation of two methods of monitoring surface cleanliness—ATP bioluminescence and traditional hygiene swabbing, Luminescence 1999.
Featherstone et al, Caries Management by Risk Assessment: Consensus Statement, Apr. 2002, CDC Journal-Feature Article, Mar. 2003 Journal of Calif. Dental Assoc.

(Continued)

*Primary Examiner* — Walter Webb
(74) *Attorney, Agent, or Firm* — John J. Connors; Connors & Assoc pc (57) ABSTRACT

A method for reducing dental disease in a patient comprises a patient wearing in the patient's mouth an appliance containing an oral care product comprising a carrier and an anti-dental disease agent with a pH above 7.0. The appliance brings the patient's teeth in direct and sustained contact with the product and is custom made for each individual patient. The oral care product is specifically prescribed and formulated for the particular dental disease of that individual patient.

2 Claims, 4 Drawing Sheets

(56) References Cited

OTHER PUBLICATIONS

Robrish, Use of Extractable Adenosine Triphosphate to Estimate the Viable Cell Mass in Dental Plaque Samples Obtained From Monkeys, American Society of Microbiology, Apr. 1978.
Kutsch-Renyer Newsletter Fall/Winter 2005,Albany,OR 97321, patient newsletter see p. 1 for relevant information.
Kutsch, VK: CAMBRA: Caries Management by Risk Assessment, art IOregon/SW Washington Doctor of Dentistry. Jan. 2004.
Kutsch, VK:How to Integrate CAMBRA into a Dental Practice, Part II, Oregon/SW Washington Doctor of Dentistry,Feb. 2004.
Steimke, A, Plaque und Karies (1983) (Englsih abstract is on p. 920).
Cheek. Paul R, www.kpchr.org/pulic/ental/mission.htm Mission Statement, Oral Health Research Program Jan. 7, 2005.
Spaeth, Dennis, Not Your Father's Dentistry, Dental Practice Report, Jul./Aug. 2003.
Zickert, Ingesgerd et al, Effect of Caries Preventative Measures in Children Highly Infected With the Bacterium *Streptacoccus* Mutans, Archs Oral Biol vol. 27 p. 861-868.

\* cited by examiner

Caries Risk Assessment Form www.carifree.com  866.928.4445

Adults/Children Age 6 and Over

Patient Name: _______________________________   Date: _____________

Instructions: Check all answers that apply.

If 1 or more Disease Indicators *or* 2 or more Risk Factors are circled, then this patient is at risk and therapeutic intervention is recommended.

1 ASSESS

DISEASE INDICATORS

|  | AT RISK | LOW RISK |
|---|---|---|
| Visible Cavitations | yes | no |
| Radiographic Lesions | yes | no |
| White Spot Lesions | yes | no |
| Cavity in Last 3 Years | yes | no |

RISK FACTORS

| Visible Plaque | yes | no |
|---|---|---|
| Inadequate Saliva Flow | yes | no |
| Hyposalivary Medications | yes | no |
| Acidic Beverages | yes | no |
| Frequent Snacking (1-3 times daily) | yes | no |
| Appliances Present | yes | no |
| Deep Pits and Fissures | yes | no |
| Other | yes | no |

TESTING

| CariScreen | 9,999 – 1,501 | 1,500 – 0 |
|---|---|---|

2 DIAGNOSE

| Risk Assessment | AT RISK | LOW RISK |
|---|---|---|

3 PRESCRIBE

Treatment Kit            Prevention Kit            Starter Kit

I understand my risk for caries based on this assessment, as well as the benefits of the recommendations for therapeutic intervention.

Release Signature: _______________________________________________

\* Based on clinically proven Caries Risk Assessment Form in the Featherstone 2003-2005 study.
\* Caries risk criteria as defined by the American Dental Association Council on Scientific Affairs, JADA August 2006.

FIG. 4

Caries Risk Assessment Form  www.carifree.com  866.928.4445

Children Age 5 and Under

Patient Name: _______________________________________  Date: _______________

Instructions: Check all answers that apply.

If 1 or more Disease Indicators *or* 2 or more Risk Factors are circled, then this patient is at risk and therapeutic intervention is recommended.

1 ASSESS

| DISEASE INDICATORS | AT RISK | LOW RISK |
|---|---|---|
| Mother/Caregiver Active Caries | yes | no |
| Socio-Economic Risk | yes | no |
| Visible Cavitations | yes | no |
| Cavity in Last 2 Years | yes | no |
| Obvious White Spot Lesions | yes | no |
| RISK FACTORS | | |
| Obvious Plaque on Teeth | yes | no |
| Gingiva Bleeds Easily | yes | no |
| Inadequate Saliva Flow | yes | no |
| Appliances Present | yes | no |
| No Dental Home/Episodic Care | yes | no |
| Developmental Problems | yes | no |
| Medications | yes | no |
| Continuous Bottle Use Not H2O | yes | no |
| Sleeps with Bottle | yes | no |
| Nurse on Demand | yes | no |
| Frequent Snacking | yes | no |
| Other | yes | no |
| TESTING | | |
| CariScreen | 1,501-9,999 | 0-1,500 |

2 DIAGNOSE

| Risk Assessment | AT RISK | LOW RISK |
|---|---|---|

3 PRESCRIBE

Xyli-Tots Oral Wipes     Xyli-Tots Mouth Spray     Xyli-Tots Tooth Gel
Xyli-Tots Lollies     Xyli-Tots Anticavity Rinse     Fluoride Varnish
CariFree Xylitol Gum I understand my risk for caries based on this assessment, as well as the benefits of the recommendations for therapeutic intervention.

Release Signature: _________________________________________________________

\* Based on clinically proven Caries Risk Assessment Form in the Featherstone 2003-2005 study.
\* Caries risk criteria as defined by the American Dental Association Council on Scientific Affairs, JADA August 2006.

FIG. 5

Perio Risk Assessment Form
Adults/Children 6 and over

Patient Name: _____________________________    Date: _____________

Instructions: Check all answers that apply.

If 1 or more Disease Indicators or 2 or more Risk Factors are circled, then this patient is at risk and therapeutic intervention is recommended.

1 ASSESS

| DISEASE INDICATORS | AT RISK | LOW RISK |
|---|---|---|
| Alveolar Bone Loss > 2mm | yes | no |
| Bleeding on Probing | yes | no |
| Tooth Loss to Perio | yes | no |
| Probing > 5 mm | yes | no |

RISK FACTORS

| | AT RISK | LOW RISK |
|---|---|---|
| Visible Plaque and Calculus | yes | no |
| Furcation Involvement > I | yes | no |
| Mobility > I | yes | no |
| Diabetes | yes | no |
| Smoking History | yes | no |
| Cardiovascular Disease | yes | no |
| Parents with CVD | yes | no |
| Parents with PDD | yes | no |

| PST | Positive | Negative |
|---|---|---|
| SPPC | Positive | Negative |
| CRP | >1.0 mg/dL | < 1.0 mg/dL |

2 DIAGNOSE

| | AT RISK | LOW RISK |
|---|---|---|
| Risk Assessment | | |
| AAP Type | 4   3   2 | 1   0 |

3 PRESCRIBE

SRP                             Prophy
LANAP                         3 months
Antimicrobials             4 months
Metronidazole/Ciprofloxacin    6 months
Periostat/Doxycycline     12 months

FIG. 6

DENTAL APPLIANCE, ORAL CARE PRODUCT AND METHOD OF PREVENTING DENTAL DISEASE

RELATED PATENT APPLICATIONS & INCORPORATION BY REFERENCE

This application claims the benefit under 35 USC 119(e) of U.S. Provisional Patent Application No. 61/133,098, entitled "Effective Treatment of Biofilm Infection to Prevent Dental Caries," filed Jun. 24, 2008. This related application is incorporated herein by reference and made a part of this application. If any conflict arises between the disclosure of the invention in this utility application and that in the related provisional application, the disclosure in this utility application shall govern. Moreover, any and all U.S. patents, U.S. patent applications, and other documents, hard copy or electronic, cited or referred to in this application are incorporated herein by reference and made a part of this application.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The words "consisting," "consists of," and other forms thereof, are intended to be equivalent in meaning and be closed ended in that an item or items following any one of these words is meant to be an exhaustive listing of such item or items and limited to only the listed item or items.

The words "substantially" and "essentially" have equivalent meanings.

BACKGROUND

Dentistry involves the restoration of natural teeth as they become carious. Dental caries is a serious disease that affects many people and is the number one childhood disease in the United States alone. Dental caries is five times more prevalent than the number two childhood disease, asthma. For years dentists and their patients have tried using fluoride, antimicrobial rinses and toothpastes, but the disease is actually getting more prevalent in spite of these approaches. Bacterial identification by DNA analysis has revealed that very distinct species of bacteria inhabit the different regions of the mouth. These findings are based on tissue receptor sites of the cell walls of the bacteria. Research has confirmed that the bacteria that cause dental diseases mainly inhabit the surfaces of the teeth in any substantial number. For example, caries causing bacteria are essentially only on the surfaces of the teeth, and periodontal disease causing bacteria are mostly on the surfaces of the teeth, but a small fraction penetrate gum tissue and some are found on the tongue.

This background discussion is not intended to be an admission of prior art.

SUMMARY

Our dental appliance, oral care product, and method has one or more of the features depicted in the embodiments discussed in the section entitled "DETAILED DESCRIPTION OF SOME ILLUSTRATIVE EMBODIMENTS." The claims that follow define our dental appliance, oral care product, and method, distinguishing them from the prior art; however, without limiting the scope of our dental appliance, oral care product, and method as expressed by these claims, in general terms, some, but not necessarily all, of their features are:

One, our oral dental appliance comprises a tray adapted to fit into the mouth of a patient that holds an anti-dental disease agent with a pH above 7.0. The tray includes a recess into which the teeth of a patient are inserted upon placing the appliance into the patient's mouth. This recess is filled with our oral care product comprising a carrier and an anti-dental disease agent. The appliance may be custom made for each individual patent. This achieves the most effective treatment delivered directly to the disease causing bacteria, since only the teeth themselves need to be targeted for treatment. A patient applies a dental practitioner's prescribed treatment directly to the patient's dental biofilm by selectively placing our product in intimate and sustained contact with the patient's teeth, gingival sulcus and supporting structures.

Two, one embodiment of our product is a viscous gel, which may include as an ingredient for suppressing caries is xylitol. The gel may include at least 10 weight percent xylitol, and typically includes substantially from 10 to 40 weight percent xylitol. The gel may comprises a mixture of components selected from the group consisting of glycerin, hydrogenated starch hydrolysate, hydroxy ethyl cellulose, natural flavors, potassium sorbate, polysorbate 20, sodium benzoate, sodium bicarbonate, sodium hydroxide, calcium acetate, water, xylitol, calcium acetate, potassium chloride, sodium hydrogen orthophosphate, sodium tetraborate, sodium hydrogen carbonate, herbal extracts, amorphous calcium phosphate, and sodium hypochlorite.

Three, our oral care product may include a buffering agent. For example, the buffering agent may be selected from the group consisting of calcium acetate, sodium hydroxide, sodium bicarbonate, sodium carbonate, potassium chloride, sodium hydrogen orthophosphate, sodium tetraborate, and sodium hydrogen carbonate. Our oral care product may also include oxidizing agent, for example, sodium hypochlorite. The pH of our oral care product may be substantially from 7.5 to 12. This range is based on the premise that a low, acidic pH in the mouth results in the acidogenic and aciduric caries producing bacterial biofilm.

Four, our method for reducing dental disease in a patient comprises the patient wearing in the patient's mouth our appliance containing our oral care product. Our appliance brings the patient's teeth in direct and sustained contact with the product. In one embodiment, our appliance is custom made for each individual patient and the oral care product is specifically prescribed and formulated for the particular dental disease of that individual patient. Our method may be used to treat a number of dental disease including caries and periodontal disease. The patient wears our appliance essentially full time. The patient only takes out our appliance to eat, clean his or her teeth—adding new gel and re-inserting our appliance. Additional biofilm metric diagnostic testing of the patient may be performed periodically to determine any change in the biofilm. Our method may reduce both the incidence of dental caries biofilm disease and the incidence of periodontal disease biofilm in the mouth of a patient wearing an orthodontic device. By applying our anti-caries and/or anti-periodontal disease product inside of the orthodontic device prior to inserting the device into the mouth of the patient, these diseases are suppressed. For caries, the patient's caries risk status is determined by a combination of a risk assessment questionnaire and a measurable biofilm metric diagnostic test. For periodontal disease, the patient's periodontal risk status is determined by a combination of a risk assessment form, a measurable biofilm metric diagnostic test, and a genetic periodontal susceptibility test that identifies the correct prescribed oral care product for a particular patient.

These features are not listed in any rank order nor is this list intended to be exhaustive.

DESCRIPTION OF THE DRAWING

Some embodiments of our dental appliance, oral care product, and method are discussed in detail in connection with the accompanying drawing, which is for illustrative purposes only. This drawing includes the following figures, with like numerals indicating like parts.

DETAILED DESCRIPTION OF SOME ILLUSTRATIVE EMBODIMENTS

Problem

The indigenous, 'normal', micro flora causes the majority of localized infectious diseases of the oral cavity (e.g., dental caries, alveolar abscesses, periodontal diseases and candidiasis). The same micro flora also protects the host from exogenous pathogens by stimulating a vigorous immune response and provides colonization resistance. How can a micro flora that supports health also cause endogenous oral disease? This paradoxical host-symbiotic relationship will be discussed within the dynamic of symbiosis. Complex microbial consortiums, existing as a biofilm, usually provide the interfaces that initiate and perpetuate the infectious assault on host tissue. The ecology of the various oral microhabitats is critical for the development of the appropriate selecting environment for pathogens. The micro-biota associated with dental caries progression and ultimately pulpal infection is primarily influenced by the prevailing pH, whereas periodontal disease appears to be more dependent on re-dox potential. Candidiasis results from host factors that favor yeast overgrowth or bacterial suppression caused by antibiotics. Oral health or disease is an adventitious event that results from microbial adaptation to prevailing conditions; prevention of endogenous oral disease can occur only when one recognizes that ecology is the heart of these host-symbiotic relationships.

General

We have developed an oral care product containing an anti-dental disease agent with an elevated pH above 7.0, for example, substantially from 7.5 to 12. In one embodiment, the product includes an oxidizing agent. A substance such as a viscous gel is used in one embodiment, and the gel may include a buffering agent. One type of anti-dental disease agent in particular is directed at eliminating the acidogenic/aciduric caries-producing bacteria in the oral biofilm. In general, the anti-dental disease agent is a neutralizing agent, creating an environment within the patient's mouth that is basic.

Rinsing, brushing, oral spraying, chewing gum and the like, which have been the normal mode of delivery for preventing caries and other dental diseases, have been less effective than once thought. Bacteria that cause dental caries and other dental diseases really only inhabit the surfaces of the teeth, the only non-shedding tissue surface of the mouth. Distinct and different species of bacteria inhabit different regions of the mouth, based on their tissue receptor sites of their cell walls. In our method the most effective treatment is delivered to these bacteria, targeting treatment directly and essentially exclusively at the teeth themselves. By using a custom-fitting appliance such as a tray filled with the gel, the most effective biofilm treatment is achieved. The patient wears the appliance substantially full time, that is all day (24 hours), only taking it out to eat, or adding new gel, or oral hygiene procedures, and then re-inserting it. The gel is periodically replaced, typically after each time the appliance is removed from the mouth. Two types of gel are typically used: One that includes an oxidizing agent and another that does not contain any significant amount of oxidizing agent. The gel including the oxidizing agent is initially used every day for the first approximately 25-35 days. This oxidizing gel kills or suppresses certain kinds of microbes normally associated with periodontal disease. Thereafter for as long as the patient desires he or she may use the gel that does not contain any significant amount of oxidizing agent. Ideally, the patient is able to wear the appliance at all times.

To get the most effective bactericidal treatment delivered directly to the teeth themselves the use of a custom fitting tray filled with a proper pH strategy gel is used. The patient gets the most effective anti-caries or other efficacious biofilm treatment using this procedure, especially when a licensed dental practitioner prescribes the specific gel. For example, in one embodiment an oral dental appliance containing a viscous gel with an elevated pH and buffering agents is worn by a patient to apply directly to the patient's dental biofilm, selectively placing the gel in intimate and sustained contact with the patient's teeth, gingival sulcus and supporting structures.

The dental appliance may use a specific type of gel that is designed to treat a diseased dental caries biofilm. The bacteria that cause dental caries are distinct for the patient and vary among the different regions of the patient's mouth, based on their tissue receptor sites of their cell walls. Also, the bacteria that cause periodontal disease are distinct for the patient and vary among the different regions of the patient's mouth, based on their tissue receptor sites of their cell walls. The bacteria that cause dental caries are distinct for the patient and have established a cariogenic biofilm using a low pH as the selection pressure for the diseased state. In addition, the bacteria that cause periodontal disease are distinct for a particular patient. They have established a periodontal diseased biofilm using an oxidation/reduction (redox) potential as the selection pressure for the diseased state. The dental appliance tray that has an elevated pH and buffering agents prescribed for the patient is directed at eliminating the acidogenic and aciduric caries-producing bacteria in the patient's oral biofilm. The elevated pH and buffering agents prescribed for the patient also contains a strong oxidizing agent directed at eliminating the oxygen reduction potential periodontal disease producing bacteria in the patient's oral biofilm. A gel with an elevated pH and buffering agents as prescribed for the patient may contain sodium hypochlorite as the strong oxidizing agent directed at eliminating the oxygen reduction potential periodontal disease producing bacteria in the patient's oral biofilm. The prescribed gel for a particular patient is identified by determining the patient's caries risk status by a combination of a risk assessment form and a measurable biofilm metric diagnostic test.

Appliance

Figures 1, 2:
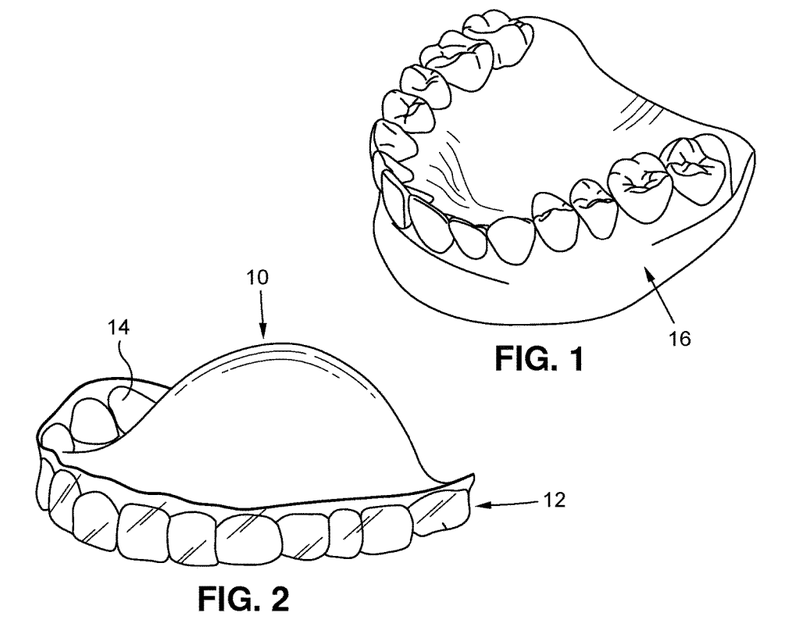
FIG. 1 depicts a plaster model of a patient's maxillary arch and teeth.
FIG. 2 is a thermo-molded clear, flexible resin tray.
Figure 3:
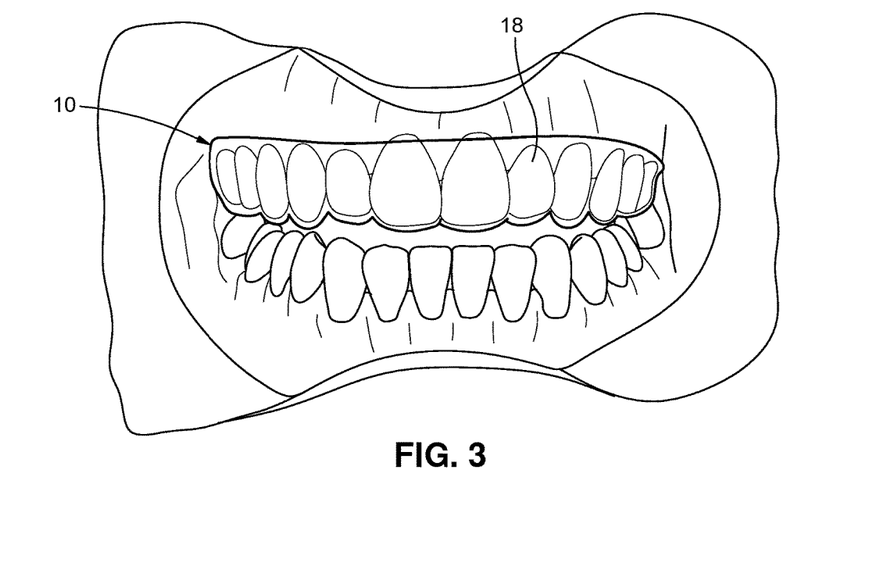
FIG. 3 depicts the tray loaded with treatment gel placed into a patient's mouth.

FIG. 2 shows one embodiment of our dental appliance 10 comprising a tray 12 with a recess 14 having an interior surface conforming to the patient's teeth so the tray fits snug against the patient's teeth 18 when inserted into the mouth as illustrated in FIG. 3. The tray 12 is custom fabricated for the individual patient, in two ways, for example: One, by taking an impression of their maxillary and/or mandibular arches and teeth and then fabricating a thin clear flexible custom tray from a variety of thermoplastic resins; two, by using a preformed stock tray that is heated and adapted closely to the patient's teeth in the mouth. FIG. 1 shows a plaster model 16 of a patient's maxillary arch and teeth from which the appliance 10 is made.

Our appliance 10 may be one from a selection of custom molded trays, esthetic appliances, thermoplastic molded trays, colored or clear thermoplastic material trays, dissolvable material tray, orthodontic retainer appliances, mouth guards, prefabricated thermo moldable materials, night guards, re-mineralization trays, prefabricated closed cell foam tray, and home "suckdown" trays. It may be made from a selection of materials including acetal resin, polypropylene, polyethylene, acrylic, polycarbonate, closed-cell foam, nylon, elastomers and thermoplastic elastomers.

In using our appliance 10, the patient follows their normal oral hygiene procedures, i.e. brushing, flossing and rinsing, and then places a small line of the prescribed neutralizing gel into one of the patient's custom tray, with enough gel to sufficiently cover all of the teeth when the tray is inserted into the mouth. The patient wears at least one appliance 10 with its tray 12 filled at all times, around the clock, only taking the appliance 10 out to eat, and perform their usual oral hygiene procedures. Each time the patient removes the appliance 10 the interior surface of the recess 14 of the tray 12 is washed out with water, brushed, and rinsed. After the appliance 10 is cleaned, the patient can reapply a fresh line of gel into the recess 14, and re-insert the appliance 10 into his or her mouth. This procedure assures that the neutralizing gel is placed in immediate and sustained contact with the patient's biofilm, thereby providing the most efficient and predictable means of treating and correcting the biofilm.

Oral Care Product

Ideally, the dentist prescribes the exact formulation of the anti-dental disease agent to be used. In general, this agent is a neutralizing agent having an elevated pH above 7.0, for example ranging substantially from 7.5 to 12. A variety of our oral care products are based on the premise of a low, acidic pH in a patient's mouth is the result of the acidogenic and aciduric caries producing bacterial biofilm. Our high pH oral care product changes this condition within the patient's mouth to kill or suppress dental disease causing microbes. Furthermore, our oral care products may contain a strong oxidizing agent. These products are based on the premise of a redox potential in the mouth results from a periodontal pathogenic bacterial biofilm. One embodiment of our oral care product is a viscous gel with an elevated pH and buffering agents. A patient applies our oral care product as prescribed for correct treatment to the biofilm directly, for example, to reduce the caries risk by suppressing the acidogenic and aciduric caries producing bacteria, thus supporting repopulation in the patient's mouth of healthy, desirable bacteria. Another embodiment of our oral care product is a viscous gel with an elevated pH, buffering agents, and a strong oxidizing agent. A patient applies this product for correct treatment to a periodontal disease producing biofilm directly to the biofilm, reducing the periodontal disease risk by suppressing the periodontal pathogens with an increase in the redox potential, thus supporting repopulation of the patient's mouth by healthy, desirable bacteria.

In our oral care products, the buffering agents may be, for example, selected from the group consisting of calcium acetate, sodium hydroxide, sodium bicarbonate, sodium carbonate, potassium chloride, sodium hydrogen orthophosphate, sodium tetraborate, sodium hydrogen carbonate.

One formulation comprises a mixture containing glycerin, hydrogenated starch hydrolysate, hydroxy ethyl cellulose, natural flavors, potassium sorbate, sodium benzoate, sodium bicarbonate, sodium hydroxide, calcium acetate, water, xylitol, herbal extracts, amorphous calcium phosphate, and sodium hypochlorite. The xylitol is especially active in suppressing caries-causing bacteria.

The following are examples of specific formulations of our oral care product:

Example I glycerin (5-20 wt %),
hydrogenated starch hydrolysate (1-10 wt %),
hydroxy ethyl cellulose (0.5-2 wt %),
natural flavors (0.1-5 wt %),
polysorbate 20 (0-3 wt %),
potassium sorbate (0.1-2 wt %),
sodium benzoate (0-2 wt %),
sodium bicarbonate (0-2 wt %),
sodium hydroxide (0-0.5 wt %),
calcium acetate (0-1.0 wt %),
water (50-75 wt %),
xylitol (10-30 wt %),
herbal extracts (0.1-2 wt %), and
amorphous calcium phosphate (0.1-2 wt %)

Example II glycerin (10 wt %),
hydrogenated starch hydrolysate (2 wt %),
hydroxy ethyl cellulose (1.45 wt %),
natural flavors (58.229 wt %),
polysorbate 20 (1 wt %),
potassium sorbate (1 wt %),
sodium benzoate (0.1 wt %),
sodium bicarbonate (0.02 wt %),
sodium hydroxide (0.001 wt %),
water (50-75 wt %), xylitol (25 wt %),
herbal extracts (0.1 wt %), and
amorphous calcium phosphate (0.1 wt %).

Example III glycerin (10 wt %),
hydrogenated starch hydrolysate (2 wt %),
hydroxy ethyl cellulose (1.45 wt %),
natural flavors (58.229 wt %),
polysorbate 20 (1 wt %),
potassium sorbate (1 wt %),
sodium benzoate (0.1 wt %),
sodium bicarbonate (0.02 wt %),
sodium hydroxide (0.001 wt %), water (50-75 wt %), xylitol (25 wt %),
herbal extracts (0.1 wt %), and
amorphous calcium phosphate (0.1 wt %).

Example IV glycerin (0-20 wt %),
hydrogenated starch hydrolysate (0-10 wt %),
hydroxy ethyl cellulose (0-2 wt %),
natural flavors (0-5 wt %),
polysorbate 20 (0-3 wt %),
potassium sorbate (0-2 wt %),
sodium benzoate (0-2 wt %),
sodium bicarbonate (0-2 wt %),
sodium hydroxide (0-0.5 wt %),
water (50-75 wt %), xylitol (0-30 wt %),
herbal extracts (0-2 wt %),
amorphous calcium phosphate (0-2 wt %),
and sodium hypochlorite 5% solution (2-10% by volume).

Method

Our method for reducing dental disease in a patient comprises the patient wearing in the patient's mouth our appliance containing our oral care product to bring the patient's teeth into direct and sustained contact with our product. The appliance is custom made for each individual patient and the oral care product is specifically prescribed and formulated by a licensed dental caregiver for the particular dental disease of that individual patient.

One embodiment of our method includes the steps of
taking DNA identification samples of caries biofilm directly from the tooth surfaces in high caries risk patients;
treating them with the tray/gel therapy for specified lengths of time; and
following up with additional DNA identification to determine the change in the biofilm.

Figure 4:
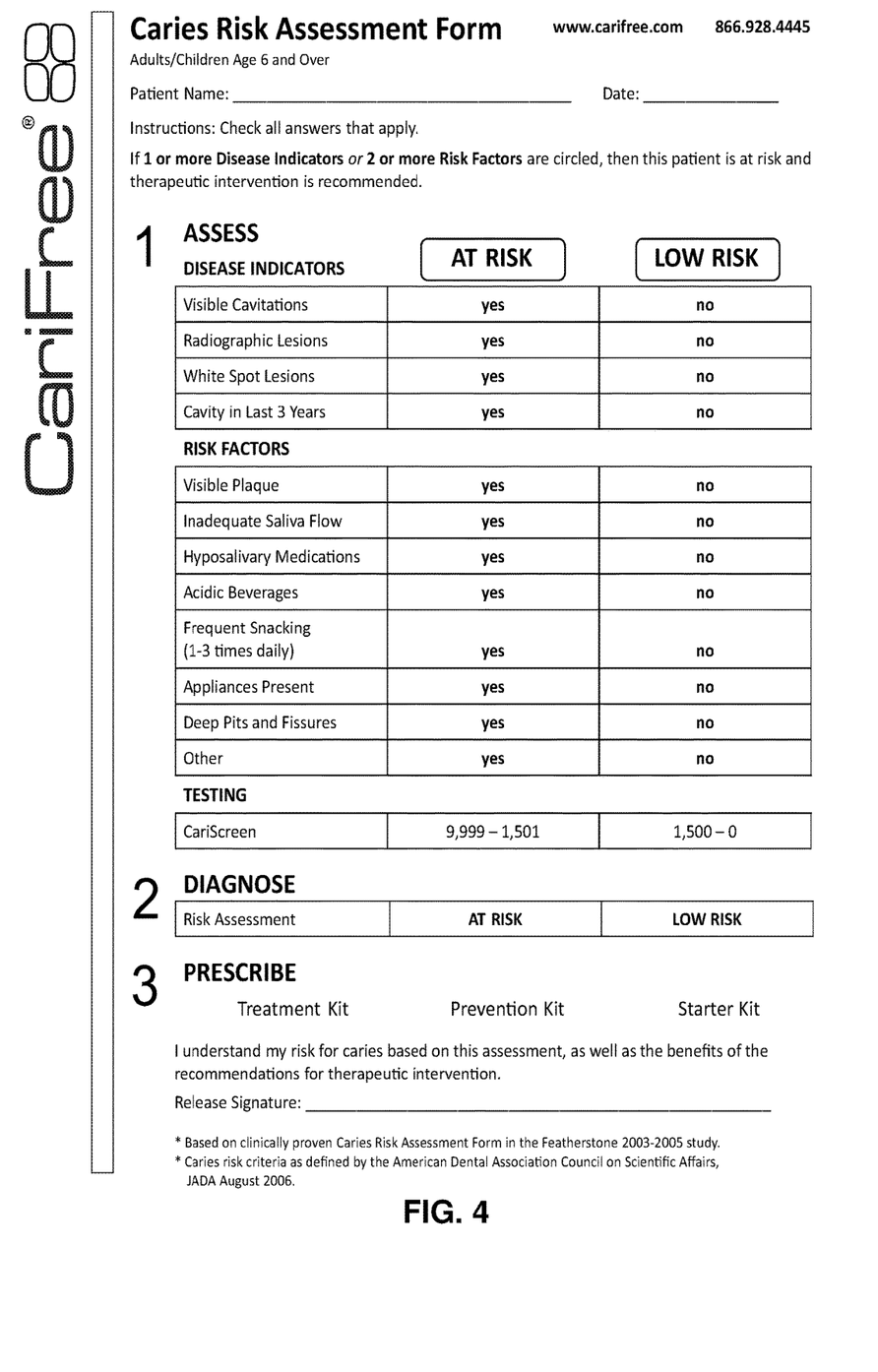
FIG. 4 is one risk assessment questionnaire for patients potentially having caries.
Figure 5:
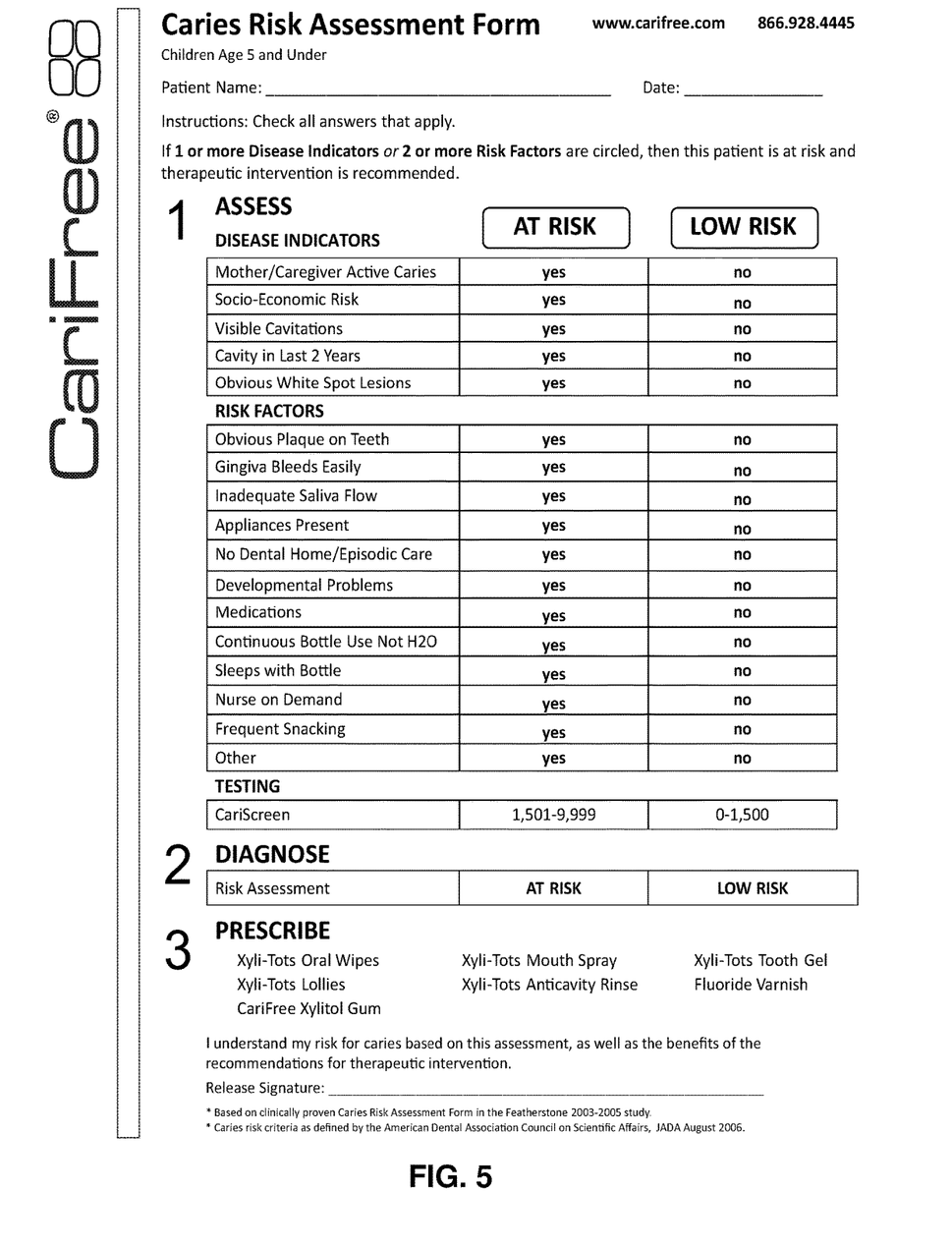
FIG. 5 is another assessment questionnaire for patients potentially having caries.

The incidence of dental caries biofilm disease in the mouth in high caries risk patients is reduced by
a) identifying such patients by performing a caries risk assessment using a risk assessment form or questionnaire as depicted in FIGS. 4 and 5;
b) identifying a dental caries biofilm using a measurable biofilm metric diagnostic test such as discussed below;
c) delivering effective anti-bacterial treatment directly and exclusively to the patient's teeth by; and
d) filling a custom fitting appliance 10 with the proper pH strategy gel and placing in the patient's mouth, and thereby delivering to such patient's mouth a very effective caries biofilm treatment.

The patient is wears our appliance 10 full time, only taking it out to eat, to clean his or her teeth, and adding new gel, and re-inserting it. The method uses additional measurable biofilm metric diagnostic testing of the patient is performed periodically to determine any change in the biofilm. For reducing the incidence of periodontal disease biofilm in the mouth of high periodontal disease risk patients, our method comprises
a) identifying such patients by performing a periodontal risk assessment using a risk assessment form or questionnaire illustrated in FIG. 6;
b) identifying a periodontal disease biofilm using a measurable biofilm metric diagnostic test such as discussed below;
c) delivering effective anti-bacterial treatment directly and exclusively to the patient's teeth, gingival sulcus and supporting structures by the patient using our appliance 10 as discussed above with the proper pH, buffering, oxidizing strategy gel to the patient's mouth, and thereby delivering to such patient's mouth a very effective periodontal disease biofilm treatment.

Figure 6:
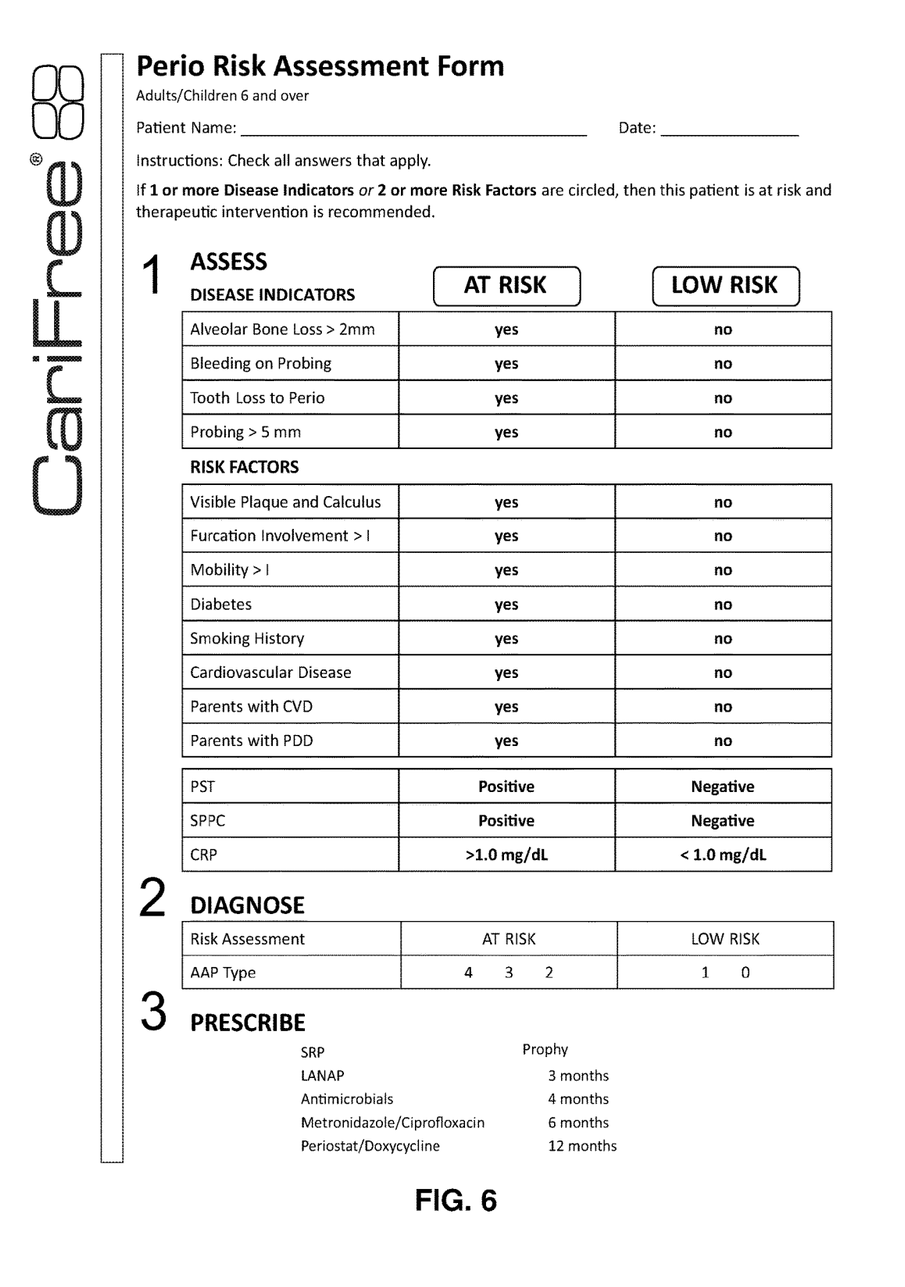
FIG. 6 is still another embodiment of a risk assessment questionnaire for patients potentially having periodontal disease.

The prescribed gel for a particular patient is identified by determining the patient's periodontal risk status by a combination of a risk assessment questionnaire depicted in FIG. 6, a measurable biofilm metric diagnostic test discussed as follows, and a genetic periodontal susceptibility test for the patient discussed as follows. Specifically, concerning the tests themselves, the measurable dental caries biofilm metric diagnostic test used is an ATP bioluminescence test. The measurable periodontal disease biofilm metric diagnostic test is a 16s rRNA gene sequence culture for periodontal pathogenic bacteria. The specific measurable periodontal pathogenic bacteria selected from the group: *Aggregatibacter actinomycetemcomitans, Porphyromonous gingivalis, Tannerella forsythia, Treponema denticola, Prevotella intermedia, peptostreptococcus micros, Fusobacterium nucleatum, Fusobacterium periodonticum, Campylobacter rectus, Eubacterium nodatum, Eikenella corrodens, Capnocytophaga gingivalis, Capnocytophaga ochracea, Capnocytophaga sputigena*. The companies that provide the periodontal metric with 16s gene sequencing of the periodontal bacteria, for example, are: Hain Diagnostics Inc, Oratec, and Oral DNA.

Yet another application of our method is the placement of a prescribed neutralizing gel into the orthodontic appliances worn by patients. This would reduce their risk for developing dental caries and at the same time reduce the unpleasant plaque build up inside of the trays while the patients are undergoing active or retentive orthodontic therapy. Intraoral trays are popularly worn for bleaching procedures, and orthodontic type appliances to move or straighten the teeth. In the case of bleaching trays, the patient may wear the tray with the bleaching product for 30 minutes at a time. In the case of the orthodontic appliance, the patient may wear the tray continuously, only removing it to eat and brush their teeth. The greatest problem for the orthodontic type trays is that they collect a tremendous amount of plaque inside the tray while the patient is wearing it, which is unpleasant and foul tasting for the patient. The plaque build-up also increases the patient's risk for dental caries. Our dental appliance avoids these problems.

An advantage of our method is in providing a better, easier, more comfortable, easy to use solution that provides direct prolonged treatment targeted specifically at the site bacteria inhabit.

SCOPE OF THE INVENTION

The above presents a description of the best mode we contemplate of carrying out our dental appliance, oral care product, and method, and of the manner and process of making and using them, in such full, clear, concise, and exact terms as to enable any person skilled in the art to make and use our dental appliance, oral care product, and method. Our dental appliance, oral care product, and method are, however, susceptible to modifications and alternate constructions from the illustrative embodiments discussed above which are fully equivalent. Consequently, it is not the intention to limit our dental appliance, oral care product, and method to the particular embodiments disclosed. On the contrary, our intention is to cover all modifications and alternate constructions coming within the spirit and scope of our dental appliance, oral care product, and method as generally expressed by the following claims, which particularly point out and distinctly claim the subject matter of our invention:

The invention claimed is:

1. A method for reducing the incidence of dental caries biofilm disease in the mouth in high caries risk patients, comprising the steps of
   (a) identifying said patients by performing a caries risk assessment,
   (b) for those individual patients identified in step (a), test the patient's biofilm for bacteria causing the caries disease using a bioluminescence test,
   (c) if the bioluminescence test indicates the presence of the bacteria causing the caries disease, formulating an effective anti-bacterial, anti-caries agent into a viscous gel, said gel including an oxidizing agent and from 10 to 40 weight percent xylitol and being buffered to have a pH from 7.5 to 12, and
   (d) delivering the gel directly and exclusively to the patient's teeth by means of a custom fitting tray including a recess having an interior surface conforming to the teeth of a patient being treated so the tray fits snug against the patient's teeth when inserted into the mouth,
   (e) prior to inserting the tray into the mouth of the patient being treated, filling the recess with enough gel to sufficiently cover all of the teeth when the tray is inserted, and then inserting the gel-filled tray into the patient's mouth to directly apply the gel to the patient's dental biofilm, selectively placing the gel in intimate and sustained contact with the patient's teeth, gingival sulcus and supporting structures, said tray being worn full time for a period from 25 to 35 days, only taking said tray out to eat, or adding new gel, or oral hygiene procedures during said period, and reinserting the tray into the patient's mouth.

2. The method of claim 1 comprising 25 weight percent xylitol and the oxidizing agent is sodium hypochlorite.

* * * * *